(12) United States Patent
Rasmussen et al.

(10) Patent No.: US 7,063,978 B2
(45) Date of Patent: Jun. 20, 2006

(54) COATED FILM LAMINATE HAVING AN ELECTRICALLY CONDUCTIVE SURFACE

(75) Inventors: Jerald K. Rasmussen, Stillwater, MN (US); William B. Knopke, New Ulm, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 595 days.

(21) Appl. No.: 10/001,307

(22) Filed: Nov. 1, 2001

(65) Prior Publication Data

US 2004/0115793 A1 Jun. 17, 2004

(51) Int. Cl.
*C12Q 1/68* (2006.01)
*C12P 19/34* (2006.01)
*C12M 1/37* (2006.01)
*C07H 21/02* (2006.01)
*C07H 21/04* (2006.01)

(52) U.S. Cl. .............. 435/287.2; 435/7.1; 435/91.1; 435/91.2; 435/6; 536/22.1; 536/23.1; 536/24.3; 536/24.31; 536/24.32; 536/24.33

(58) Field of Classification Search ............. 435/6, 435/7.1, 91.1, 91.2, 287.1; 536/22.1, 23.1, 536/24.3–24.33; 428/328
See application file for complete search history.

(56) References Cited

U.S. PATENT DOCUMENTS

| | | | |
|---|---|---|---|
| 4,332,075 A | * | 6/1982 | Ota et al. .................... 29/571 |
| 4,539,256 A | | 9/1985 | Shipman |
| 4,726,989 A | | 2/1988 | Mrozinski |
| 4,957,943 A | | 9/1990 | McAllister et al. |
| 5,278,377 A | | 1/1994 | Tsai |
| 5,446,270 A | | 8/1995 | Chamberlain et al. |
| 5,529,708 A | | 6/1996 | Palmgrem et al. |
| 5,925,455 A | | 7/1999 | Bruzzone et al. |
| 6,060,327 A | * | 5/2000 | Keen ......................... 436/518 |
| 6,395,483 B1 | * | 5/2002 | Patil et al. .................. 435/6 |
| 6,468,785 B1 | * | 10/2002 | Wang et al. ............ 435/287.2 |
| 6,593,089 B1 | * | 7/2003 | Patil et al. .................. 435/6 |

FOREIGN PATENT DOCUMENTS

| | | |
|---|---|---|
| WO | WO 99/53319 | 10/1999 |
| WO | WO 00/77523 | 12/2000 |
| WO | WO 01/06011 | 1/2001 |
| WO | WO 01/16370 | 3/2001 |
| WO | WO/01/29547 * | 4/2001 |

OTHER PUBLICATIONS

W.J. Feast et al., Polymer, 37(22), 5017 (1996).

D.S. Minehan et al., "Kinetics of DNA Binding to Electrically Conducting Polypyrrole Films", *Macromolecules* 1994, 27, 777–783.

* cited by examiner

*Primary Examiner*—Jeffrey Siew
(74) *Attorney, Agent, or Firm*—Christopher D. Gram; Robert W. Sprague

(57) ABSTRACT

Articles including a polymeric substrate and an electrically conductive surface are provided. Methods of making and using such articles also are provided.

34 Claims, 1 Drawing Sheet

COATED FILM LAMINATE HAVING AN ELECTRICALLY CONDUCTIVE SURFACE

BACKGROUND

Analysis and detection of biological molecules typically involve placing a sample onto an immobilizing membrane and then performing steps to detect the presence of or quantitate one or more particular biological molecules in the sample. A sample may be spotted directly onto the immobilizing membrane or transferred from a matrix to the immobilizing membrane by blotting. Such a transfer may be necessary because the matrix can be unsuited for many of the biological or chemical assays known to those skilled in the art. The transfer may be passive or energy-driven, such as by an electric current. Once the sample has been transferred to the membrane, the desired assay can be performed on the immobilized sample.

Methods of transferring biological molecules to immobilizing membranes are known in the art. For example, polynucleotide sequences may be transferred from a gel made of agarose or polyacrylamnide to a cellulose-derived or nylon membrane. Similarly, proteins may be transferred from an SDS-polyacrylamide gel to a cellulose-derived or nylon membrane. Immobilizing membranes made from nylon or cellulose-derived materials are porous and permit the transfer of polynucleotides or proteins through a variety of processes, some of which are energy independent and some of which, such as electroblotting, are energy-driven.

Many assays performed on biological molecules can be performed on a miniaturized scale. Many of these assays use samples and reagents that oftentimes are expensive or difficult to obtain. Accordingly, assays performed on a miniaturized scale are desirable because they may dramatically reduce the amount of sample and reagents required for performing the assay. Miniaturized assays are especially desired when an expensive or limited sample can be concentrated, thereby reducing the amount of the sample required for the assay while simultaneously increasing the sensitivity, accuracy or efficiency of the assay. In addition to the reduction of volume, miniaturization allows hundreds or thousands of assays to be performed simultaneously.

Some assays may include electrical manipulation of one or more samples, e.g., excitation of a sample to generate a desired visible signal, selective heating of particular samples, controlled transport of a fluid sample, and the like.

A heat-shrinkable film such as that reported in International Publication No. WO 99/53319, published Oct. 21, 1999, permits samples to be concentrated for miniaturized assays. Such a film may be used, for example, as a substrate to which reactants, e.g., peptides or nucleotides, may be affixed, thereby forming a riniaturized array. What is needed is an article including a shrinkable film that can be used to efficiently immobilize molecules transferred to the laminate for subsequent detection or assay. There is a further need that the article include an electrically conductive surface.

SUMMARY

The present invention provides an article having an electrically conductive surface that can be used to immobilize molecules including reactants or sample molecules that have been transferred to the article. The article is a laminate including a shrinkable substrate such as a polyethylene shrink film. The article also includes an electrically conductive coating layer. The electrically conductive coating layer may include, for example, one or more electrically conductive polymers. Molecules may be affixed to the article by techniques known for constructing arrays. For example, molecules may be spotted using, e.g., pins, ink jets or capillaries. Alternatively, molecules may be transferred from a matrix, such as a gel for separating sample molecules, to the article by an energy-independent process or by a process that is energy-dependent, such as electroblotting. The electrically conductive surface may reversibly affix molecules (i.e., reactants or sample molecules) to the article, such as by forming one or more ionic bonds between the surface coating and the molecules. Alternatively, certain embodiments of the present invention possess a coating that is capable of forming one or more covalent bonds with a molecule. Because the article is shrinkable, molecules that have been transferred to the article may be concentrated for use in a miniaturized assay.

The electrically conductive coating may form a pattern on the surface of the article, thereby providing an electrical circuit. The patterned electrically conductive coating may be applied to the article prior to shrinking the substrate so that the resulting electrical circuit is miniaturized when the substrate is shrunk. Reactants or sample molecules also may be affixed to the article prior to shrinking. Thus, after shrinking, the resulting article may provide both a miniaturized electrical circuit and concentrated reactants or sample molecules.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

Definitions

For purposes of this invention, the following definitions shall have the meanings set forth.

"A" or "an" refers to one or more of the recited elements.

"Affix" shall include any mode of attaching biological molecules to a substrate. Such modes shall include, without limitation, covalent bonding, ionic bonding, and adherence, such as with an adhesive, physical entrapment, and adsorption. This may or may not require the use of linking agents.

"Density" shall mean a measure of quantity per unit projected area of a substrate, such as, for example, molecules per square centimeter.

"Doped" shall mean, in the context of an electrically conductive material, that electrons have been introduced through reduction or removed through oxidation.

"Heat-relaxable" or "heat-shrinkable" shall mean, in the context of a material such as a substrate, that the material undergoes some relaxation or shrinkage in at least one dimension in response to the transmission of thermal energy into the material.

"Linking agent" shall mean any chemical species capable of affixing a "Molecule" to a substrate. Linking agents can be covalently bonded to the substrate or can be provided by a polymeric coating thereon.

"Molecule," as defined herein, shall be construed broadly to mean any molecule, compound, composition or complex, either naturally occurring or synthesized, that can be affixed to a substrate. Molecules include, without limitation, polypeptides, fatty acids, polynucleotides, carbohydrates, polysaccharides, hormones, steroids, lipids, vitamins, bacteria, viruses, pharmaceuticals, and metabolites.

"Polynucleotide" shall mean any polymer of nucleotides without regard to its length. Thus, for example, ribonucleotides and deoxyribonucleotides are each included in the definition of polynucleotide as used herein, whether in single- or double-stranded form. A polynucleotide, as used herein, may be obtained directly from a natural source or may be synthesized using recombinant, enzymatic or chemical techniques. A polynucleotide may be linear or circular in topology and can be, for example, a vector such as an expression vector, cloning vector or any type of plasrnid, or any fragment thereof.

"Polypeptide" shall mean any polymer of amino acids without regard to its length. Thus, for example, the terms peptide, oligopeptide, protein, enzyme, and fragments thereof are all included within the definition of polypeptide as used herein. The term also includes polypeptides that have been modified by post-translational expression or synthetic processes yielding, for example, glycosylated, acetylated, phosphorylated polypeptides, or peptide nucleic acids. Accordingly, a polypeptide may be obtained directly from a natural source or may be synthesized using enzymatic or chemical techniques.

"Polysaccharide" shall mean any polymer of saccharides without regard to its size. The term also includes classes of molecules that are polymers of saccharides in combination with other monomers such as amino acids, nucleotides, and any polymers thereof. Such classes of molecules include, but are not limited to, glycosaminoglycans, proteoglycans and glycolipids.

"Projected surface area" shall mean the surface area for a surface as is calculated with respect to the plane encompassing the "x" and "y" axes of the surface.

"Reactant" shall mean any chemical molecule, compound, composition or complex, either naturally occurring or synthesized, that is capable of binding an analyte in a sample of interest either alone or in conjunction with a molecule or compound that assists in binding the analyte to the substrate, such as, for example, a coenzyme. The reactants of the present invention are useful for chemical or biochemical measurement, detection or separation. Accordingly, the term "Reactant" specifically excludes molecules, compounds, compositions or complexes, such as ink, that do not bind analytes as described above. Examples of reactants include, without limitation, amino acids, nucleic acids, including oligonucleotides and cDNA, carbohydrates, and proteins such as enzymes and antibodies.

"Recoverable" means, in the context of a material, such as a substrate, that the material is stretched and capable of subsequently recovering at least one dimension, preferably to substantially its original size.

"Relaxable" shall mean, in the context of a material such as a substrate, that the material is capable of relaxing or shrinking, in at least one dimension. Preferably, shrinkage occurs by at least about 10%.

"Shrinkable," "shrinking" or "shrunk" shall mean, in the context of a material such as a substrate, that the material is capable of being, is, or has been decreased in its length in at least one dimension, whether by recovery, relaxation, or any other means.

"Topographical surface area" shall mean the area of a surface as calculated with respect to the planes encompassing the "x", "y" and "z" axes of the surface.

"Undulations" or "undulated" shall mean convoluted, wave-like forms. For purposes of this invention, it is preferred that an undulated surface includes undulations that do not form a regular pattern. "Undulations" or "undulated" does not include structures such as reservoirs or microwells that are created by methods such as for example printing, embossing, casting, molding, laserscribing, photolithography, etching, mechanical scratching, or scoring.

DETAILED DESCRIPTION OF THE INVENTION

The present invention provides an article having an electrically conductive surface that can be used to immobilize molecules that have been transferred to the article. The article includes a shrinkable substrate such as a polyethylene shrink film. The article also includes an electrically conductive coating layer disposed on at least a portion of the substrate. The coating layer may include, for example, an electrically conductive polymer made from one or more unsaturated monomers such as aromatic compounds or compounds that may be polymerized to form a conjugated polymer, e.g., acetylene. Because the article is shrinkable, molecules such as reactants or sample molecules that have been transferred to the article may be concentrated for use in a miniaturized assay. Molecules may be transferred to the article by any process such as spotting, passive blotting or electrophoretic transfer, namely electroblotting, although these are not necessarily the only possible transfer processes. The electrically conductive polymeric surface may reversibly or covalently affix molecules to the article. Because the article is shrinkable, molecules that have been transferred to the article may be concentrated and electrical circuits applied to the substrate may be miniaturized.

The Article

Figure 1A:
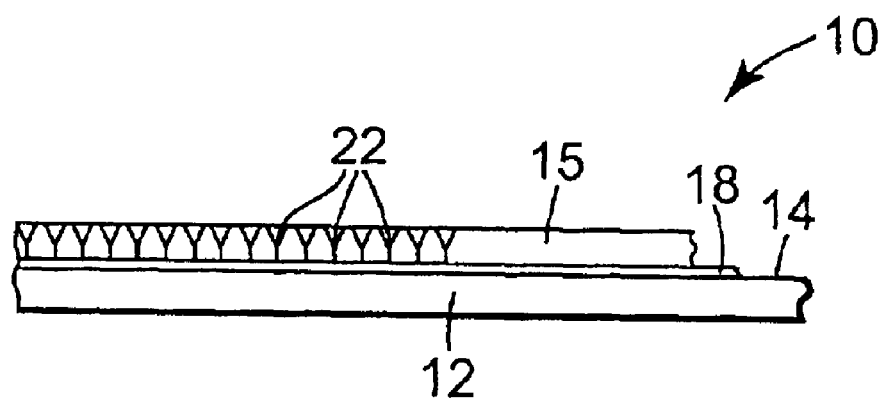
FIG. 1a is a side view of one embodiment of the article of present invention prior to relaxation of the substrate thereof.
Figure 1B:
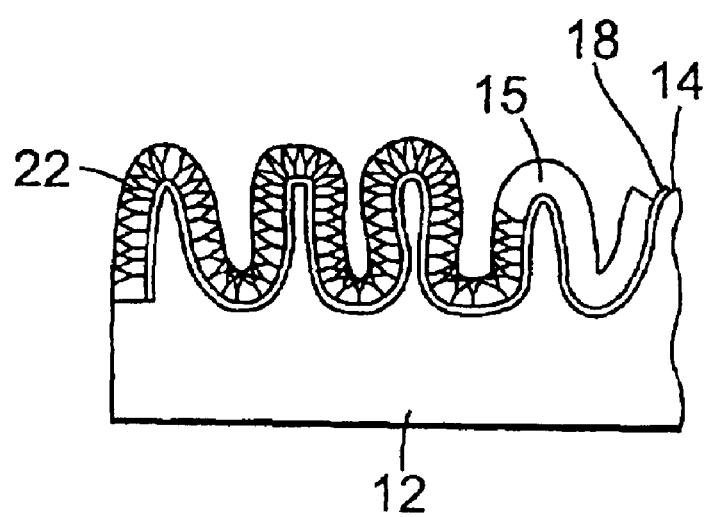
FIG. 1b is a side view of the article of FIG. 1a subsequent to relaxation of the substrate thereof.

With reference to FIGS. 1a and 1b, the article 10 generally includes a substrate 12 with at least one major surface 14 having a surface area. The major surface 14 may be generally smooth or may include undulations. The substrate 12 may be any number of shapes. The shape of the substrate 12 is not limiting, so long as the substrate 12 provides a base for applying a surface coating 15 thereon, as described more fully below.

The substrate 12 is a shrinkable, polymeric material. Accordingly, the substrate 12 has a projected surface area and a topographical surface area. Prior to shrinking, the projected surface area and the topographical surface area are substantially equivalent. When shrunk, however, the surface of the substrate 12 may become undulated. In this case, the topographical surface area becomes greater than the projected surface area.

A surface coating 15 is at least partially adhered, directly or indirectly, to the substrate 12 and has a generally smooth appearance, shown in FIG. 1a. The surface coating 15 has a projected surface area and a topographical surface area. Accordingly, the projected surface area and the topographical surface area of the surface coating 15 are substantially equivalent prior to shrinking the substrate 12. As described more fully below, upon shrinking of the substrate 12, the topographical surface area of the surface coating 15 becomes greater than the projected surface area of the surface coating 15. The article 10 includes a surface coating 15 that is capable of exhibiting a topographical surface area that greatly exceeds the projected surface area. The topographical surface area of the surface coating 15 may be at least about five times greater than the projected surface area. In one embodiment, the topographical surface area is at least fifteen times greater than the projected surface area.

Upon shrinking of the substrate 12, the surface coating 15 may become undulated as depicted in FIG. 1b. While the undulations generally are irregular with respect to any discernable pattern, a regular pattern of undulations may be obtained. The adhesion of the surface coating 15 to the substrate 12 should be sufficient to prevent its total delamination from the substrate 12. When the article 10 has an undulated surface, a degree of delamination may actually occur and still provide a useful article for use in the claimed method. However, the degree of delamination should not be so great as to interfere with assays being conducted on the article 10 or result in effective loss of the surface coating 15 from the substrate 12.

The article 10 is capable of exhibiting high topographical surface areas. The high topographical surface area offers opportunities for increasing the signal strength of certain assays. When shrunk, the undulated surface permits more molecules to be concentrated in a given projected surface area compared to transferring molecules to a relatively flat, unshrinkable surface. Also, in the case where transferred molecules are affixed prior to shrinking the substrate 12, the spatial relationship of the affixed molecules to one another on the surface is fixed. Upon shrinking of the substrate 12, the surface of the surface coating 15 becomes undulated, in effect increasing the density of affixed molecules with respect to the projected surface area but substantially maintaining their relative separation due to the topographical surface area of the surface coating 15. This spacing allows presentation of a high density of molecules at or near the surface of the surface coating 15 while minimizing potential steric crowding. This, in turn, facilitates rapid interaction kinetics with prospective assay reagents.

Substrates

The substrate 12 of the article 10 is a polymeric material. The material of the substrate 12 is selected with regard to the application for the resulting article. For example, if fluorescence will be used to detect the transferred sample molecules, the material used for the substrate 12 may be selected to exhibit low background fluorescence. Also, the substrate 12 material can be selected so that it is compatible with the reagents and conditions of the assays such as temperature, solvents and pH.

Many polymeric materials may be suitable for use in the article 10. For certain embodiments having a high topographical surface area, one skilled in the art can select materials capable of being oriented, i.e., films that shrink at least in one direction within the film plane when energy such as heat is applied to the film for a specified period of time. Elastomeric materials are also suitable for use as a substrate 12 in the article 10. Elastomeric materials include materials that are stretched in at least one direction prior to coating, constrained in the stretched state during coating, and then allowed to recover, thereby reducing the projected surface area of the substrate surface from the stretched state. Thus, herein, a relaxable substrate includes an oriented film and a recoverable substrate includes an elastomeric material.

With respect to oriented films, relaxation need not be equal in any two orthogonal directions within the film plane. In one embodiment, relaxation of the substrate 12, and therefore the article 10, is substantially uniform. In this embodiment, the oriented film relaxes in substantially the same amount in each direction, regardless of position on the film plane. If the oriented film employed does not exhibit substantially uniform relaxation characteristics, a registration indicator may be employed to register relative positions on the relaxed article.

The substrate 12 provides a surface 14 upon which additional layers or other films or coatings (e.g., polymeric coatings, mask layers, etc.) may be disposed. Upon relaxation or recovery of the substrate 12, the substrate 12 provides support and integrity to the surface coating 15, or other films or coatings (e.g., polymeric coatings, mask layers, etc.) disposed thereon.

Oriented films suitable for use as a substrate 12 in the article 10 include, but are not limited to, biaxially oriented low-density polyethylenes, biaxially oriented linear low-density polyethylenes, and biaxially oriented ultra low-density polyethylenes. Biaxially oriented films exhibit shrinkage in two orthogonal in-plane directions (hereafter referred to as the "x" and "y" directions). Other oriented films that may be suitable for use in the claimed article include uniaxially, biaxially, or multiaxially oriented films made by any process known to the art, including, but not limited to: melt-orientation; the blown film, bubble, double-bubble, and tubular processes; length orientation; the process of tentering; extension over a mandrel; thermoforming; and blow molding. Polymers which may be employed in such films include, but are not limited to: polyethylenes, including high density polyethylene, low density polyethylene, linear low density polyethylene, ultra low density polyethylene, and copolymers of ethylene (including ethylene propylene copolymers and ethylene vinyl acetate copolymers); polyolefins, including isotactic polypropylene, syndiotactic polypropylene, and polymethylpentene; polyacetals; polyamides, including nylon 6 and nylon 6,6; polyesters, including polyethylene terephthalate, polybutylene terephthalate, and polyethylene naphthalate; halogenated polymers, including polyvinyl chloride, polyvinylidene chloride, polychlorotrifluoroethylene, polyvinyl fluoride, and polyvinylidene fluoride; styrene polymers, including general purpose polystyrene, syndiotactic polystyrene, and high impact polystyrene; cellulose esters, including cellulose acetate and cellulose propionate; polyketones, including polyetheretherketone and copolymers and terpolymers of carbon monoxide with ethylene and/or propylene; polycarbonates, including the polycarbonate of bisphenol A; phenyl-ring polymers, including polyphenylene sulfide; polysulfones; polyurethanes; polymers of acrylic and methacrylic acids and their esters; ionomers; and copolymers, blends, or layered structures of any of the above-named polymers. Oriented films of any of these polymers may be optionally cross-linked.

Examples of elastomeric materials that may be suitable for use as the substrate 12 in the coated article 10 include natural rubber, polyisoprenes, polycmloroprene, polyisobutylenes, polybutenes, nitrites, polyurethanes, silicones, random copolymers and terpolymers (such as ethylene-propylene copolymers and ethylene-propylene-diene monomer terpolymers), and block copolymers.

Electrically Conductive Surface Coating

An electrically conductive surface coating 15 is at least partially adhered, directly or indirectly, to at least a portion of the substrate 12 to form the article 10 of the present invention. The surface coating 15 may be indirectly adhered to the substrate 12 through an optional layer 18 that may be desirable for certain applications. The surface coating 15 may be disposed over substantially the entire projected surface area of the article or, alternatively, may be disposed over only a portion of the projected surface area of the article, e.g., to form a pattern providing electrical conductivity to one or more particular areas of the article surface. The electrically conductive surface coating 15 may be cationic or anionic. The surface coating 15 additionally may be crosslinked.

The surface coating 15 includes an electrically conductive polymer. The electrically conductive polymer may be any conductive polymer known in the art. Conductive polymers may be prepared from conjugated polymers or copolymers, i.e., polymers that have π-electron delocalization along their backbone. Conjugated polymers may be made conductive by doping, i.e., having extra electrons or, alternatively, "holes" injected into them. A "hole" is a position where an electron is missing. When such a hole is filled by an electron jumping in from a neighboring position, a new hole is created at that neighboring position, thereby allowing a charge to migrate. Thus, the presence of either extra electrons or holes enables the polymer to conduct electricity. A discussion of conjugated polymers that are useful in this invention can be found in W. J. Feast et al, Polymer, 37(22), 5017 (1996).

Suitable electrically conducting polymers include doped polymers and copolymers made from monomers having at least one moiety providing π-electron delocalization. Suitable moieties include, but are not limited to, monocyclic aromatic hydrocarbons such as aniline or benzene; polycyclic aromatic compounds such a naphthalene; 5-membered aromatic heterocyclic compounds such as pyrrole, thiophene or furan; 6-membered aromatic heterocyclic compounds such as pyridine or thiobenzene. Suitable moieties also include any substituted analogs of any of the foregoing. For example, electrically conductive polymers may be made from monomers having pyrrole or thiophene moieties containing substituents in the 3-position, 4-position, or both. Suitable electrically conductive polymers also may be made from acyclic unsaturated hydrocarbon monomers including, but not limited to, acetylene, polyacetylenes, or substituted analogs thereof. Furthermore, suitable conductive polymers may include two or more of any of the foregoing monomers in any combination. For example, the electrically conductive polymer may include a plurality of different aromatic moieties. Alternatively, the electrically conductive polymer may include aromatic moieties linked by acyclic unsaturated hydrocarbon chains.

The surface coating 15 may be preformed and applied to the surface of the substrate 12. In one embodiment, the surface coating 15 may be prepared by dissolving a preformed electrically conductive polymer in an appropriate solvent. A layer of the polymer solution may be applied to the substrate 12 and the solvent allowed to evaporate. Application of the solution may be by any conventional coating means.

Alternatively, the surface coating 15 can be made in situ by applying a dopant solution to the substrate 12, drying the dopant solution, and then permitting monomers from a monomer solution to polymerize within the dopant solution, thereby forming the electrically conductive polymer. Polymerization of the monomer solution in this manner is facilitated, in part, by preparing the monomer solution to be volatile, i.e., having a vapor phase. The monomer solution may be made volatile by, for example, selection of solvents, heating, or both. The substrate 12, coated with the dopant solution, may be placed in contact with the vapor phase of the monomer solution, thereby permitting polymerization of the monomer solution to occur within the dopant solution. Suitable dopants useful in this invention include, but are not limited to, ferric chloride, cupric chloride, titanium tetrachloride, nickel chloride, and arsenic pentafluoride.

FIG. 1a depicts an article 10 having a surface coating 15 that includes linking agents 22 capable of immobilizing or affixing molecules that have been transferred to the article. Alternatively, linking agents 22 may be provided in an overcoating layer disposed over all or part of the surface coating 15. If desired, more than one type of linking agent 22 may be used. When present, linking agents 22 may be adhered directly or indirectly to the substrate 12. For example, a layer of linking agents can be affixed subsequent to providing the surface coating 15, which is disposed on a substrate 12. When the surface coating 15 covers substantially the entire projected surface area of the substrate 12, the inking agents 22 will generally be adhered to the substrate 12 indirectly. However, when the surface coating 15 covers only a portion of the surface 14, and no other intervening layers (e.g., optional layers described below) are present, a portion of the linking agents 22 may be adhered directly to the substrate 12 while linking agents 22 overcoating the surface coating 15 are adhered to the substrate 12 indirectly. Alternatively, linking agents can be an integral component of the surface coating 15, as depicted in FIG. 1a. For example, the surface coating 15 may be prepared from 3-pyrrolyl butyric acid, in which case the pyrrole moiety provides electrical conductivity to the surface coating and the butyric acid moiety may serve as a linking agent. Any number of processes known in the art may be used to introduce the linking agents 22 to be affixed to the surface coating 15 or the substrate 12. It is understood that the mode of affixation may vary in accordance with the linking agents 22 employed.

The type of linking agent 22 that may be used in the present invention may vary according to the application and the molecule, i.e., reactants or sample molecules, to be affixed, detected or quantified. Linking agents 22 suitable for covalent immobilization of reactants or transferred sample molecules include azlactone moieties such as those provided by copolymers reported in International Publication No. WO 99/53319, published Oct. 21, 1999. Other useful linking agents 22 are also reported in the same publication. Azlactone moieties are useful because these moieties are suitable for reaction with many different classes of molecules, including polypeptides and nucleotides. Azlactone moieties also generally exhibit high reactivity with molecules transferred to the article or with other coatings comprising different linking agents, such as those described below. Azlactone moieties are also generally hydrolytically stable and therefore have a relatively long shelf life when used in the article 10 of the present invention. In one embodiment of the article 10 of the claimed method includes a surface coating 15 including both electrically conductive copolymers, such as those described above, and azlactone copolymers. In an alternative embodiment of the article 10 of the present invention, azlactone moieties are provided in a polymeric overcoating disposed on the surface coating 15.

Surprisingly, certain articles of the present invention having electrically conductive surfaces provide an additional advantage compared to similar articles lacking an electrically conductive coating. Articles having an electrically conductive coating have been observed to bind a greater number of molecules compared to similar articles without an electrically conductive coating when spotted with equivalent solutions. As shown in Example 18 below, a polypyrrole-coated article may affix about 20-fold more molecules per spot than an azlactone-coated article when each article is spotted a solution of 10 μM oligonucleotide. Thus, articles of the present invention provide more efficient immobilization of reactants, sample molecules, or other assay reagents. Therefore, assays performed using articles of the present invention may be performed using less of the reactant, sample molecule, or other reagent, thereby reducing consumption of resources and, for some assays, generation of hazardous waste.

In certain embodiments, the surface coating 15 may provide masking properties to the article. For example, the surface coating 15 may reduce or prevent the transmission of electromagnetic energy from beneath the analyte, e.g., from the substrate, that is similar to the electromagnetic signal emitted by the desired analyte in response to the excitation energy. In either case, the electromagnetic signals emitted from the surface of the film can generally be attributed to excitation of the sample molecule transferred to the film rather than the underlying substrate 12 or other portions of the film. Certain embodiments of the present invention include surface coatings 15 that may provide lower levels of background signals than masking layers previously described. In other embodiments, the surface coating 15 may be sensitive to electromagnetic energy, thereby promoting desirable shrink properties to an article 10 having a heat-shrinkable polymeric substrate.

Alternatively, masking properties, electromagnetic energy sensitivity, or both may be provided by an optional layer 18, shown in FIG. 1a underlying the surface coating 15. Materials suitable for use in an optional mask layer 18 include, but are not limited to, masking materials reported in International Publication No. WO 01/16370, published Mar. 8, 2001. An optional layer 18 including electromagnetic energy sensitive material can take a variety of forms as reported in U.S. patent application Ser. No. 09/459,418, filed on Dec. 9, 1999. Examples of some suitable materials include, but are not limited to, those reported in U.S. Pat. No. 5,278,377 (Tsai); U.S. Pat. No. 5,446,270 (Chamberlain et al.); U.S. Pat. No. 5,529,708 (Palmgren et al.); and U.S. Pat. No. 5,925,455 (Bruzzone et al.). The electromagnetic energy sensitive material may be the same or different than the mask layer material, if a mask layer is present.

Although the optional layer 18 is depicted as being in direct contact with the substrate 12, one or more intervening layers may be located between the optional layer 18 and substrate 12, provided that the electromagnetic energy sensitive material, if present in the optional layer 18, is in thermal communication with the heat-relaxable material in the substrate 12 such that thermal energy in optional layer 18 is conducted to the substrate 12.

Methods of Relaxation/Recovery and Functionalization

Relaxation and recovery of the films making up the substrate 12 can be accomplished using the methods reported in International Publication No. WO 99/53319, published Oct. 21, 1999. Oriented films exhibit an area shrinkage reduction that is dependent in part on the degree of elongation of the film during orientation thereof. The area shrinkage reduction is a measure of the area shrinkage of the film from its oriented, pre-shrunken dimensions to its dimensions after energy has been applied to shrink the film. For example, a 10 cm×10 cm (100 cm$^2$ area) film that shrinks fifty percent (50%) in the "x" direction and fifty percent (50%) in the "y" direction after the application of sufficient heat will be reduced to 5 cm×5 cm (25 cm$^2$ area), thereby exhibiting an area shrinkage reduction of seventy-five percent (75%). An area shrinkage reduction of about twenty-five percent (25%) is suitable for the article 10, but an area shrinkage reduction of more than about seventy-five percent (75%) may be achieved in certain embodiments, thereby producing a article with very high-densities of reactants or transferred sample molecules.

When miniaturization is desired, the substrate 12, and therefore the article 10, may be shrunk, i.e., a substrate 12 comprising an oriented film may be relaxed or a substrate 12 comprising a stretched elastomeric film may be recovered. The relative positions of the spots or bands occupied by the reactants or transferred sample molecules prior to shrinking the article should be maintained after the article is shrunk. However, the density of the reactants or sample molecules may be increased dramatically.

With respect to oriented films, the reduction may be effected by the application of heat, although other modes of relaxing oriented films can be used. The mode of size alteration, such as the application of heat, can be selected so that it does not substantially impair the activity of the molecules, e.g., reactants or sample molecules, affixed to the article. For example, fairly high heat may be employed to shrink a substrate 12 having oligonucleotides affixed thereto (approximately 150 degrees Celsius) without destroying the ability to have subsequent DNA hybridization occur with the oligonucleotides.

With respect to elastomeric materials, the reduction of the projected surface area may be achieved by releasing the force that is holding the material in the stretched condition. The substrate 12 may be subsequently treated to hold the substrate 12 in the shrunken format. Alternatively, a backing or other physical means may be applied to the substrate 12 to hold it in the size-altered format.

The relative positions of the molecules affixed to the article are maintained when the article 10 of the present invention is shrunk. However, shrinking the article 10 may increase the density of the molecules affixed thereto by a substantial factor. The density of molecules affixed to the article 10 may be increased 4-fold, 10-fold, or even greater than 20-fold by using the articles and methods of the present invention.

Increasing the density of the molecules affixed to the article 10 is advantageous where an intensified detection signal is desired, such as, for example, when fluorescent, absorbent, or chemiluminescent labels are used as detection signals. Moreover, increasing the density of the molecules affixed to the article 10 means that a smaller amount of the sample is required to elicit a signal substantially functionally equivalent, for example, to performing the same assay in a multi-well plate. Additionally, less assay media may be required to perform an assay on the reduced surface area occupied by molecules concentrated on the shrunken article 10 according to the present invention compared to performing the same assay, for example, in a multi-well plate or on a non-shrinkable immobilizing membrane.

Transfer of Sample Molecules to the Article

Molecules such as reactants or sample molecules can be transferred to the article 10 by any suitable process. For example, molecules may be spotted directly onto a desired area of the article 10. Alternatively, molecules may be transferred from a matrix to the article 10 by passive blotting. For example, sample molecules that have been run through an agarose or polyacrylamide gel may be transferred and affixed to the article 10. The matrix may or may not separate one or more sample molecules from one another. The matrix is placed in contact with the article and the matrix and article 10 are assembled into a typical blotting configuration well known in the art, such as between layers of filter paper. Alternatively, the matrix and article are assembled in a commercially available blotting apparatus according to the apparatus manufacturer's instructions. During the blotting process, the sample molecules are transferred from the matrix to the article 10 in register with their positions in the matrix. Thus, the article 10 contains a replica of the pattern of sample molecules that was generated as the sample molecules were run through the matrix.

Alternatively, molecules may be transferred from the matrix to the article 10 by electroblotting, i.e., blotting driven by an electric current. The matrix and the article 10 are assembled in an electroblotting apparatus and the apparatus is run according to the apparatus manufacturer's instructions. Once applied, the electric current drives migration of the molecules from the matrix to the article 10. As in passive blotting, molecules are transferred to the article 10 in register with their relative positions in the matrix. Thus, an electroblotted article 10 will also contain a replica of the pattern of molecules that was generated as the molecules were run through the matrix.

Whichever transfer process is used, molecules from a single gel may be transferred to more than one article 10 as described above. Therefore, one can obtain a series of articles, each with an identical replica blot of the pattern of molecules present in the matrix. The ability to obtain multiple identical blots from one matrix, using the article of the present invention, is advantageous for subsequent functional analysis of the transferred molecules. For example, one may produce a series of identical blots of a set of separated proteins from a sample comprising a mixture of proteins. One blot might be probed with one or more specific monoclonal antibodies, another one developed for carbohydrate functionality, another for a specific enzyme activity such as phosphatase or phosphorylase, or any of a number of other assays. After evaluating these various assays one would still have the matrix as a source for recovery of the untransferred proteins for further processing.

This is an exceptionally useful application of the present invention as it allows one to perform several different analyses in parallel on replica blots of sample molecules from a single gel. Because each blot is in register with every other blot, individual sample molecules may be identified by their relative positions on each blot and those relative positions will be the same as the relative positions occupied by the sample molecules in the original gel. Thus, results from the series of parallel assays may provide data that can be used, for example, to identify or characterize individual sample molecules in the blots. Once identified or characterized, the position of any of the sample molecule remaining in the original gel is known.

Additionally, because the sample molecules can be concentrated by shrinking the article 10 after the sample molecules are transferred, less of the sample molecule may need to be transferred in order to perform the desired assays, thereby preserving more of each of the matrix-bound sample molecules for further processing, if desired. Also, less assay reagent may be needed to perform a particular assay on the transferred sample molecules after they have been concentrated as a result of shrinking the article 10, resulting in reduced costs. As an example, proteins from a 2-D protein gel may be transferred to a article 10, then shrunk to produce a replica that has, for example, a projected surface area $\frac{1}{20}^{th}$ that of the of the original gel. The shrunken article 10 thus may require a smaller volume of reagents to perform a particular assay compared to performing the same assay on proteins transferred to a non-shrinkable immobilizing membrane.

While characterized above with reference to identification and analysis of proteins, the article of the present invention may be used with similar advantages with respect to identification and analysis of polynucleotides, polysaccharides or any other class of biological or non-biological molecules. Accordingly, the article of the present invention may be used to identify and analyze polynucleotides or polysaccharides in a manner similar to that described above for the transfer, identification and analysis of polypeptides, e.g., proteins.

Alternative Applications for Articles with Electrically Conductive Coatings

In addition to providing an immobilizing surface for biological molecules, the articles of the present invention may be useful for a wide variety of applications. For example, articles of the present invention may provide miniaturized circuit boards, exclusive of such use in biological arrays, as described above. Articles of the present invention also may provide polymeric batteries, antistatic coatings, electromagnetic shielding of circuits, or corrosion protection. In certain environments, articles of the present invention may be useful for replacing copper wiring or used in creating nanowires. Certain articles with electrically conductive coatings may act as microwave absorbents, thereby being useful as radar-invisible coatings. Articles having electrically conductive surfaces also may be useful for fabricating light-emitting diodes, field-effect transistors, and electroluminescent displays.

Article of the present invention also may be used as surfaces to grow nerve cells. Certain articles having electrically conductive polymers may be used in manufacturing artificial muscles or in conjunction with artificial skin grafts to provide electric stimuli to muscle tissues. Articles of the present invention may be useful in bio-electric monitors, e.g., heart monitors or devices for detection of damaged nervous tissue.

EXAMPLES

The following examples have been selected merely to further illustrate features, advantages, and other details of the invention. It is to be expressly understood, however, that while the examples serve this purpose, the particular ingredients and amounts used as well as other conditions and details are not to be construed in a matter that would unduly limit the scope of this invention. Unless otherwise indicated, all ratios and percentages provided herein are by weight.

Examples 1–8

Polypyrrole Coated on Polyethylene Shrink Film

Example 1

A dopant solution of 10% ferric chloride, 90% ethanol was prepared. A small aliquot (1–2 ml) was applied to a piece of biaxially oriented polyethylene shrink film (CRYOVAC D-955 Film, W. R. Grace & Co., Duncan, S.C.) and then immediately coated with a #10 Meyer (wire wound) bar. The polyethylene shrink film had been subjected to corona treatment in a nitrogen atmosphere at a film speed of 10 m/min, a power of 550 W, and a surface energy of 1.0 J/cm$^2$. The polyethylene film coated with the dopant solution was oven dried at 50° C. for two minute before being attached to a solid support (e.g., an aluminum pan). Once fixed to the solid support the sample film was placed in contact with the vapor phase (about 3.0 cm above the liquid surface) of a monomer solution containing 10% pyrrole monomer, 20% toluene and 70% heptane. A thin, back film of doped polypyrrole formed on the polyethylene shrink film almost instantaneously at ambient conditions. The polyethylene film coated with polypyrrole was dried in an oven at 50° C. for a few minutes before being rinsed with deionized water. The polypyrrole coated shrink film was then dried again at 50° C. for several minutes to remove excess water. The appearance of the polymerized film is described in Table A.

Examples 2–8

Pyrrole-coated polyethylene shrink film was prepared as described above in Example 1, except that the dopant solution, monomer solution, or both were modified by changing he ratios of selected components as indicated in Table A. The appearance of the resulting polymerized films is described in Table A.

TABLE A

Appearance of Polypyrrole Films

| Example | Dopant* | Monomer^ | Appearance of Polypyrrole coatings |
|---|---|---|---|
| 1 | 10/90 | 10/20/70 | Dark black, semi-uniform |
| 2 | 5/95 | 10/20/70 | Gray-black, uniform |
| 3 | 1/99 | 10/20/70 | Faint gray, non-uniform |
| 4 | 10/90 | 5/22.5/72.5 | Gray-black, semi-uniform |
| 5 | 10/90 | 1/24.5/74.5 | Faint black, semi-uniform |
| 6 | 10/90 | 20/15/65 | Dark black, uniform |
| 7 | 5/95 | 20/15/65 | Gray-black, uniform |
| 8 | 5/95 | 5/22.5/72.5 | Black, semi-uniform |

*% ferric chloride/% ethanol.
^% pyrrole/% toluene/% heptane.

Examples 9–10

Patterned Conductive Coating on Polyethylene Shrink Film

A dopant solution of 5% ferric chloride, 95% ethanol was prepared. A disposable transfer pipette was used to spot various patterns of the dopant solution onto nitrogen-corona treated polyethylene shrink film. The dopant solution was applied to the film as: straight parallel lines, intersecting perpendicular lines (gridlines), large dots, small dots, or "t" designs. The volume of dopant solution used for each pattern ranged from 1 µl to 2 ml. Once potted with the dopant solution, the polyethylene films were oven dried for two minutes at 50° C. The films were then attached to a solid support (e.g., an aluminum pan) and placed in contact with the vapor phase of a monomer solution of 10% pyrrole monomer, 20% toluene and 70% heptane. Polymerization was observed to occur instantly. Each spotted pattern was visible as thin, black coating of polypyrrole formed on the polyethylene shrink film. After polymerization had significantly slowed, i.e., when the blackening of the films had subsided, the films were removed and oven dried for a few minutes at 50° C. The polyethylene films containing polypyrrole designs were then rinsed with deionized water and oven dried again at 50° C.

The films were shrunk, thereby producing miniaturized conductive patterns that maintained good adhesion to the polyethylene film in the shrunken configuration.

Example 10

A piece of nitrogen corona-treated polyethylene shrink film was obtained and fixed with long, narrow strips of Scotch Brand Magic Mending Tape (Minnesota Mining and Manufacturing Co., St. Paul, Minn.) to form a pattern of ordered, straight parallel lines. The strips were spaced approximately 0.5 cm to 1.0 cm apart. Once the strips of tape were in place, a dopant solution of 5% ferric chloride, 95% ethanol was prepared. A small aliquot of dopant solution was applied to the polyethylene shrink film containing the tape and coated onto the film with a #10 Meyer bar. The polyethylene film was oven dried for two minutes at 50° C. before the tape strips were removed, thus leaving uniform, straight, parallel lines of dopant solution on the polyethylene film. The polyethylene film was fixed to a solid support and placed in contact with the vapor phase of a monomer solution of 10% pyrrole monomer, 20% toluene and 70% heptane. Polymerization was visible instantly as darkened parallel lines of polypyrrole on the polyethylene shrink film. After polymerization was completed to the desired extent, i.e., when the darkening of the film had subsided, the polyethylene film coated with parallel lines were oven dried at 50° C. for a few minutes. The film was then removed and rinsed with deionized water. The film was then oven dried again after rinsing at 50° C. for several minutes to remove excess water.

Examples 11–16

Polythiophene Coated on Polyethylene Shrink Film

Example 11

A dopant solution of 10% ferric chloride, 90% ethanol was prepared and a small aliquot (1–2 ml) was applied and coated onto a piece of nitrogen-corona treated polyethylene shrink film with a #10 Meyer bar. A monomer solution of 10% thiophene monomer, 20% toluene and 70% heptane was preheated to 84° C. in an exhaust hood. The film was fixed to a solid support and placed directly over the preheated monomer solution. Crude polymerization was visible as darkening of the film. The film was then oven dried at 50° C. for several minutes. The film was then shrunk in an oven set at 178° C. for 45 seconds. Evidence of polymerization could be better seen post-shrinking. The appearance of the polymerized, shrunken film is described in Table B.

Examples 12–16

Polythiophene-coated polyethylene shrink film was prepared as described in Example 11, except that the monomer solution was modified as indicated for each example in Table B. The appearance of the polymerized, shrunken films is described in Table B.

TABLE B

Appearance of Polythiophene Films

| Example | Monomer Solution | Appearance of film |
|---|---|---|
| 11 | 10% thiophene/20% toluene/70% heptane | Black, non-uniform |
| 12 | 20% thiophene/40% toluene/40% heptane | Black, semi-uniform |
| 13 | 25% thiophene/75% toluene | Gray-black color, uniform |
| 14 | 10% thiophene/20% xylene/70% heptane | Black, non-uniform |
| 15 | 20% thiophene/40% xylene/40% heptane | Gray-black, uniform |
| 16 | 25% thiophene/75% xylene | Gray-black, uniform |

Example 17

Protein Immobilization by Electroblotting on Polypyrrole-coated Polyethylene Shrink Film A piece of film was prepared as in Example 2, above. A 1.5% solution of nitrocellulose in methyl ethyl ketone (MEK) was made to overcoat the polypyrrole-coated polyethylene shrink film. A small aliquot (1–2 ml) of the nitrocellulose solution was coated onto the polypyrrole-coated film with a #10 Meyer bar. The polypyrrole/nitrocellulose-coated film was allowed to air dry for two minutes before being oven dried at 50° C. for 30 minutes.

Polyacrylamnide gel electrophoresis was performed on a 5 μg sample of ProtA-FITC (Protein A-fluorescein isothiocyanate conjugate) and a 5 μg sample of BSA-FITC (bovine serum albumin-fluorescein isothiocyanate conjugate) using a precast 4–15% Tris-HCl READY GEL (Bio-Rad Laboratories, Hercules, Calif.) in a Mini TRANS-BLOT cell (Bio-Rad). Power was supplied by a POWER PAC 1000 (Bio-Rad). Electrophoresis was conducted in a buffer of 25 mM Tris/192 mM glycine/0.1% SDS, pH 8.3.

The polypyrrole/nitrocellulose-coated film and the polyacrylamide gel containing the electrophoresed protein samples were assembled in a Semi-dry Trans-blot (BioRad) electroblotting apparatus according to the manufacturer's instructions. A blotting buffer of 48 mM Tris/39 mM glycine in 20% methanol, pH 9.2 was used. The blotting apparatus ran for 45 minutes while set at 20 volts and 500 mA, then the transfer was completed by allowing the assembled apparatus to stand overnight.

The transferred proteins were detected on the polypyrrole/nitrocellulose coated polyethylene shrink film by detecting fluorescence at 328 nm with a TRANSILLUMINATOR ultraviolet light detection instrument, model LM-20E (UVP, Upland, Calif.).

Example 18

DNA Coupling on Polypyrrole-coated Polyethylene Shrink Film

A piece of polyethylene shrink film was coated as described in Example 2. A second piece of polyethylene shrink film (CRYOVAC D955 Film, W. R. Grace & Co., Duncan, S.C.) without an electrically conductive coating was prepared as a comparative example. This film included a titanium mask layer having an optical density of 0.36 and was prepared by the method reported in International Publication No. WO 01/16370. The Ti-coated film was overcoated using a standard extrusion coating method with an azlactone copolymer solution having 0.75% solids in isopropanol and enough ethylenediamine to provide 10% crosslinking. Thus, the comparative film is referred to as being azlactone-coated in Table C.

An oligonucleotide (obtained from Applied Biosystems, Foster City, Calif.) having the following sequence:

5'-C6 amino-CGT GGG TCT TGC TCA AAC GAT TCG T-3' was radioactively labeled with $^{32}$p using a DNA 3'-End Labeling Kit (Boehringer Mannheim, Indianapolis, Ind.) according to the manufacturer's instructions. Labeled oligonucleotide was spiked into unlabeled oligonucleotide to provide a ratio of about 1:30,000 labeled:unlabeled probe. Samples were prepared having oligonucleotide concentrations of 100 μM, 10.0 μM and 1.0 μM in 100 mM CHES (cyclobexylaminoethanesulfonic acid) buffer, pH 9.0. The 10.0 μM and 1.0 μM samples were each spotted five times onto the polypyrrole-coated film in 1 μl volumetric amounts. The 100 μM and 10.0 μM samples were each spotted five times onto the comparative film.

The spotted films were allowed to stand for two hours in darkness at room temperature and humidity, then were rinsed with deionized water for several minutes. Coupled oligonucleotides were detected on the films by screening, as described below. A dilution series of standards of known concentration was prepared from the labeled oligonucleotide solution, spotted onto a separate film and screened. The films were screened overnight underneath a CYCLONE Storage Phosphor Screen (Packard Instrument Company, Meriden, Conn.). The screened image was inserted into a scanning carousel and viewed with a CYCLONE Storage Phosphor Scanner (Packard Instrument Co.) and analyzed with OPTI-QUANT imaging software, version 3.10 (Packard Instrument Co.). The analysis provided the number of radiolabeled oligonucleotide molecules that coupled to each of the films. Coupling data are summarized in Table C.

TABLE C

Total Molecules of Oligonucleotide Coupled per Spot to Polypyrrole-Coated Polyethylene Film and Azlactone-Coated Polyethylene Film

| Film | Oligonucleotide Concentration (μM) | | |
|---|---|---|---|
| | 100 | 10 | 1.0 |
| Polypyrrole-coated | N/A | $5.63 \times 10^{12}$ | $5.29 \times 10^{11}$ |
| Azlactone-coated | $1.61 \times 10^{12}$ | $2.80 \times 10^{11}$ | N/A |

Examples 19–21

DNA Hybridization on Polypyrrole-coated Polyethylene Shrink Film

Example 19

A piece of polyethylene shrink film was coated as described in Example 2. The polypyrrole-coated film was used as a substrate for DNA hybridization.

The oligonucleotide of Example 18 was used, unlabeled, to prepared samples having oligonucleotide concentrations of 10.0 μM, 1.0 μM, 0.1 μM, and 0.01 μM in 100 mM CHES buffer, pH 9.0. Each sample was spotted three times onto the polypyrrole-coated film in 1 μl volumetric amounts. The spotted film underwent coupling for two hours in darkness at room temperature and humidity, then rinsed in deionized water for several minutes. The excess water remaining on the sample film was removed with compressed air. The coupled film was shrunk between two pieces of TEFLON-coated mesh fabric in an oven at 178° C. for 45 seconds. The film was then removed and pressed flat with two glass slides. Dust particles were removed from the shrunken film with compressed air.

Hybridization solution was prepared from 28.2 ml stock 5.0 M TMACl (tetramethylammonium chloride), 4.70 ml stock 0.5 M MES (morpholinoethanesulfonic acid) buffer, 470 μl stock sheared salmon sperm DNA (10 mg/mL), 1.17 ml stock bovine serum albumin (20 mg/ml), and 470 μl 1% Triton-X 100. The coupled, shrunken film was placed in a scintillation vial with 4.0 ml of hybridization solution to undergo a pre-hybridization step. The scintillation vial containing the coupled, shrunken film and pre-hybridization solution was agitated in an oven set at 50° C. for one hour. After the pre-hybridization step, excess hybridization solution was removed from the film with compressed air.

A target oligonucleotide (Applied Biosystems), complementary to the unlabeled probe oligonucleotide, having the following sequence:

5'-ACG AAT CGT TTG AGC AAG ACC CAC G-3' was radioactively labeled with $^{32}$p using a DNA 5'-End Labeling Kit (Boehringer Mannheim) according to the manufacturer's instructions. Labeled oligonucleotide was spiked into unlabeled oligonucleotide to provide a ratio of about 1:10 labeled:unlabeled target. The coupled, shrunken film was placed into a new scintillation vial containing 20.0 μl of oligonucleotide solution obtained above and 3.98 ml hybridization solution to provide a final target oligonucleotide concentration of 100 pM. Hybridization was allowed to take place overnight in an oven set at 50° C. while being agitated.

The hybridized film was removed from the scintillation vial and excess hybridization solution was removed with compressed air. Hybridization was detected by screening overnight on a CYCLONE Storage Phosphor Screen (Packard Instrument Co.). The screened image was loaded onto a scanning carousel, viewed with a CYCLONE Storage Phosphor Scanner (Packard Instrument Co.) and analyzed with OPTIQUANT software, version 3.10 (Packard Instrument Co.). A dilution series of standards was prepared from the labeled oligonucleotide solution to permit quantitation. Image analysis of the film and standards showed that hybridization occurred and provided the number of radiolabeled complementary oligonucleotides that hybridized to the unlabeled target oligonucleotides that had been spotted on the film. This experiment was run in duplicate and the mean results of the duplicate runs are shown in Table D.

Example 20

A piece of polyethylene shrink film was coated in the same manner as described in Example 2, except that an overcoat of 70% dimethylacrylamide/30% vinyl dimethylazlactone (DMANDM) copolymer (1.5% solids) that had been 10% cross-linked with ethylenediamine was applied with a Meyer (wire wound) bar.

The azlactone overcoat solution was obtained by diluting 2.00 g of stock 70% DMA/30% VDM azlactone copolymer (29.5% solids) with 37.33 g of isopropanol followed by mixing, to which 14.2 μl of ethylenediamine was added to achieve 10% cross-linking. A small amount (1–2 ml) of dilute azlactone copolymer solution was applied to the polypyrrole coated polyethylene shrink film with a pipette and coated with a #10 Meyer bar. After the overcoat had been applied, the film was dried in an oven at 50° C. for 1 hour. After drying, the film was removed and hydrolyzed by submerging it in deionized water for 30 minutes. The film was then used as a substrate for DNA hybridization as described in Example 19. The results are shown in Table D.

Example 21

A piece of polyethylene shrink film was prepared as described in Example 20, except that the aziactone overcoat was not hydrolyzed in deionized water. The film was then used as a substrate for DNA hybridization as described in Example 19. The results are shown in Table D.

TABLE D

Total Molecules of Radiolabeled Oligonucleotide Hybridized per Spot to Probe Oligonudeotides

| | Concentration of Spotted Probe Oligonucleotide (μM) | | | |
|---|---|---|---|---|
| Example | 10.0 | 1.0 | 0.1 | 0.01 |
| 19 | $1.55 \times 10^8$ | $1.52 \times 10^8$ | $5.77 \times 10^7$ | $7.61 \times 10^6$ |
| 20 | $6.09 \times 10^8$ | $1.58 \times 10^8$ | $6.19 \times 10^7$ | $8.98 \times 10^6$ |
| 21 | $1.32 \times 10^9$ | $2.89 \times 10^9$ | $2.51 \times 10^8$ | $4.3 \times 10^7$ |

Example 22–24

Solution Polymerization of Pyrrole onto Various Substrate Materials

Example 22

A dopant solution of 10% ferric chloride, 90% ethanol was prepared. A piece of polyethylene shrink film was cut and allowed to soak in a small volume (10 ml) of dopant solution for a few minutes. The polyethylene film was removed after soaking and was dried at room temperature for several minutes. After drying, the ferric chloride coated polyethylene film was placed into a monomer solution of 10% pyrrole, 20% toluene and 70% heptane for a few minutes. Polymerization was observed to occur instantly as large, random, black polypyrrole regions formed on the shrink film. The film was removed from the monomer solution and allowed to air dry.

Example 23

A dopant solution of 10% ferric chloride, 90% ethanol was prepared. A piece of porous nitrocellulose transfer blotting membrane (Bio-Rad Laboratories, Hercules, Calif.) was cut and allowed to soak in the dopant solution for a few minutes. The nitrocellulose membrane was removed after soaking and was dried in an oven for two minutes at 50° C. The coated membrane was then submerged and allowed to soak in a monomer solution of 10% pyrrole, 20% toluene and 70% heptane for several minutes. Polymerization was observed to occur instantly as the nitrocellulose membrane blackened uniformly. The membrane was removed from solution and oven dried again at 50° C. for several minutes. The polypyrrole-coated nitrocellulose membrane was then rinsed with deionized water for two minutes and oven-dried a final time at 50° C. for several minutes.

Example 24

A polypropylene thermally induced phase separation (TIPS) membrane was coated with polypyrrole by the method described in Example 23. TIPS membrane materials are described in detail in U.S. Pat. No. 4,726,989 (Mrozinski), U.S. Pat. No. 4,957,943 (McAllister et al), and U.S. Pat. No. 4,539,256 (Shipman). The polypyrrole formed a black, uniform coating on the polypropylene TIPS membrane.

Example 25

Synthesis of Polypyrrole within an Aziactone Copolymer Network

A dopant solution of 10% ferric chloride, 90% ethanol was prepared. A small aliquot (1–2 ml) of dopant solution was applied to a piece of polyethylene shrink film and coated onto the film with a #10 Meyer bar. The coated film was oven-dried for five minutes at 50° C.

70% DMA/30% VDM copolymer (29.5% solids) was diluted in isopropyl alcohol to 1.0% solids. Pyrrole was then added to the dilute copolymer solution to create a 10% pyrrole/90% azlactone copolymer weight fraction. Ethylenediamine was then added to the pyrrole/azlactone solution (to achieve 10% cross-linking of the azlactone copolymer, after taking into account the weight fraction of the solution), and mixed for one minute A small volume of monomer/copolymer solution (1–2 ml) was then applied to the dried film and coated with a #10 Meyer bar. The Meyer bar provided an evenly distributed coating layer of the pyrrole/azlactone copolymer solution. Polymerization of the pyrrole was observed to occur after several minutes within the copolymer network as the film blackened. The film was then dried in an oven at 50° C. for one hour.

Example 26

Electrical Conductivity of Polypyrrole-coated Film

A piece of polyethylene shrink film was prepared as described in Example 2. A second piece of polyethylene shrink film was prepared as described in Example 20. An uncoated piece of polyethylene shrink film was obtained as a control.

Electrical conductance of a material is the reciprocal of the material's electrical resistance. The resistance of the polypyrrole coatings was measured by placing each probe of a multimeter onto the surface of the coating 1 inch apart and recording the initial reading displayed on the meter. Ten separate readings were recorded and averaged for each of the three films. The results are summarized in Table E.

TABLE E

Electrical Resistance of Polypyrrole-coated Films

| Film | Electrical Resistance |
| --- | --- |
| Polpyrrole-coated (Example 2) | 190.3 k-ohms |
| Polypyrrole/azlactone-coated (Example 20) | 277.3 k-ohms |
| Uncoated | >30 megohms |

Example 27

Masking Properties of Polypyrrole-coated Film

Polypyrrole-coated film was obtained as described in Example 2, along with comparative (Ti masked) film from Example 18. Shrunk and unshrunk samples of each film were mounted on glass microscope slides, then scanned with a GenePix 4000A Microarray Scanner (Axon Instruments, Foster City, Calif.) to determine the level of background fluorescence present in the films. GenePix software, version 2.0, was used to analyze the images at two different excitation wavelengths, 532 (Cy3) and 635 (Cy5) nm. Results are shown in Table F.

TABLE F

Average Background Fluorescent Intensity Measurements[a]

| Excitation Wavelength | | |
| --- | --- | --- |
| | Preshrunk Polypyrrole Ctg. | Preshrunk Titanium Ctg. |
| 532 nm (Cy3) | 2793.2 | 3361.7 |
| 635 nm (Cy5) | 752.8 | N/A |
| | Shrunk Polypyrrole Ctg. | Shrunk Titanium Ctg. |
| 532 nm (Cy3) | 409.5[b] | 2343.6 |
| | 362.3[c] | |
| 635 nm (Cy5) | 135.4 | N/A |

[a]All measurements were preformed at a PMT setting of 800 on the Axon Scanner Instrument.
[b]Trial 1.
[c]Trial 2.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An article comprising:
    a polymeric substrate; and
    an electrically conductive coating disposed on at least a portion of the substrate and having a projected surface area and a topographical surface area wherein the topographical surface area is greater than the projected surface area, wherein the coating comprises at least one electrically conductive polymer that composes at least one moiety having π-electron delocalization.

2. The article of claim 1 wherein the moiety comprises a monocyclic aromatic hydrocarbon, a polycyclic aromatic hydrocarbon, a 5-membered aromatic heterocyclic compound, a 6-membered aromatic heterocyclic compound, or any substituted analog of any of the foregoing.

3. The article of claim 2 wherein the moiety comprises a 5-membered aromatic heterocyclic compound selected from pyrrole or thiophene.

4. The article of claim 2 wherein the moiety comprises aniline.

5. The article of claim 1 wherein the coating further comprises one or more azlactone moieties.

6. The article of claim 1 wherein the electrically conductive coating is disposed on a portion of the substrate in a defined pattern.

7. The article of claim 1 wherein the electrically conductive coating provides an electrical circuit.

8. The article of claim 1 further comprising a polymeric coating comprising azlactone moieties adhered to at least a portion of the substrate.

9. The article of claim 1 wherein the polymeric substrate comprises a relaxed oriented film or a recovered elastomeric material.

10. An array comprising:
    an article that comprises a polymeric substrate and an electrically conductive coating disposed on at least a portion of the substrate, and having a projected surface area and a topographical surface area wherein the topographical surface area is greater than the projected surface area, wherein the coating comprises at least one electrically conductive polymer that comprises at least one moiety having π-electron delocalization; and
    one or more reactants affixed to the electrically conductive coating.

11. The array of claim 10 wherein at least one reactant is a polypeptide, a polynucleotide, a polysaccharide, or any combination thereof.

12. The array of claim 10 wherein the reactants are affixed to the polymeric coating to form an ordered array.

13. A method of making a coated article, the method comprising:
    providing a shrinkable polymeric substrate;
    coating at least a portion of the polymeric substrate with a dopant;
    permitting a monomer to contact the dopant, thereby forming an electrically conductive coating; and
    shrinking the substrate.

14. The method of claim 13 wherein the monomer is acetylene, a polyacetylene, or a substituted analog thereof.

15. The method of claim 13 wherein the monomer comprises at least one moiety having π-electron delocalization.

16. The method of claim 15 wherein the moiety comprises a monocyclic aromatic hydrocarbon, a polycyclic aromatic hydrocarbon, a 5-membered aromatic heterocyclic compound, a 6-membered aromatic heterocyclic compound, or any substituted analog of any of the foregoing.

17. The method of claim 13 wherein the monomer is provided in a monomer solution.

18. The method of claim 17 wherein the monomer solution comprises, by weight, about 20% toluene, about 70% heptane, and about 10% 5-membered aromatic heterocyclic compound.

19. The method of claim 18 wherein the 5-membered aromatic heterocyclic compound comprises pyrrole or thiophene.

20. The method of claim 17 wherein the monomer solution comprises a vapor phase and the monomer is provided in the vapor phase.

21. The method of claim 13 further comprising affixing at least one reactant to the electrically conductive coating.

22. The method of claim 21 wherein at least one reactant comprises a polypeptide, a polynucleotide, a polysaccharide, or any combination thereof.

23. The method of claim 13 wherein the electrically conductive polymeric coating comprises at least one azlactone moiety.

24. The method of claim 13 further comprising:
applying an overcoating comprising azlactone moieties to at least a portion of the article.

25. The method of claim 24 further comprising:
affixing at least one reactant to the aziactone overcoating.

26. An article comprising:
a polymeric substrate; and
a polymeric coating comprising at least one electrically conductive polymer disposed on at least a portion of the substrate and having a projected surface area and a topographical surface area wherein the topographical surface area is greater than the projected surface area, wherein the electrically conductive polymer comprises acetylene, a polyacetylene, or a substituted analog thereof.

27. The article of claim 26 wherein the polymeric coating further comprises one or more azlactone moieties.

28. The article of claim 26 wherein the electrically conductive coating is disposed on a portion of the substrate in a defined pattern.

29. The article of claim 26 wherein the electrically conductive coating provides an electrical circuit.

30. The article of claim 26 further comprising a polymeric coating comprising azlactone moieties adhered to at least a portion of the substrate.

31. The article of claim 26 wherein the polymeric substrate comprises a relaxed oriented film or a recovered elastomeric material.

32. An array comprising:
an article that comprises a polymeric substrate and a polymeric coating comprising at least one electrically conductive polymer disposed on at least a portion of the substrate and having a projected surface area and a topographical surface area wherein the topographical surface area is greater than the projected surface area, wherein the electrically conductive polymer comprises acetylene, a polyacetylene, or a substituted analog thereof; and
one or more reactants affixed to the electrically conductive coating.

33. The array of claim 32 wherein at least one reactant is a polypeptide, a polynucleotide, a polysaccharide, or any combination thereof.

34. The array of claim 32 wherein the reactants are affixed to the polymeric coating to form an ordered array.

* * * * *

UNITED STATES PATENT AND TRADEMARK OFFICE
CERTIFICATE OF CORRECTION

PATENT NO. : 7,063,978 B2
APPLICATION NO. : 10/001307
DATED : June 20, 2006
INVENTOR(S) : Jerald K. Rasmussen It is certified that error appears in the above-identified patent and that said Letters Patent is hereby corrected as shown below:

Column 1
Line 23, Delete "polyacrylamnide" and insert in place thereof -- polyacrylamide --;

Column 1
Line 53, Delete "riniaturized" and insert in place thereof -- miniaturized --;

Column 3
Line 10, Delete "plasrnid," and insert in place thereof -- plasmid, --;

Column 6
Line 53, Delete "polycmloroprene," and insert in place thereof -- polychloroprene, --;

Column 6
Line 54, Delete "nitrites," and insert in place thereof -- nitriles, --;

Column 8
Line 13, Delete "inking" and insert in place thereof -- linking --;

Column 8
Line 23, Delete "3-pyrrolyl butyric" and insert in place thereof -- 3-pyrrolyl-4-butyric --;

Column 9
Line 52, Delete "Intermational" and insert in place thereof -- International --;

Column 10
Line 42, Delete "chemiluniinescent" and insert in place thereof -- chemiluminescent --;

Column 12
Line 67, Delete "back" and insert in place thereof -- black --;

Column 13
Line 10, Delete "Pyrrole" and insert in place thereof -- Polypyrrole --;

Column 13
Line 13, After the word "changing" delete "he" and insert in place thereof -- the --;

Column 13
Line 44, Delete "potted" and insert in place thereof -- spotted --;

Column 15
Line 7, Delete "Polyacrylamnide" and insert in place thereof -- Polyacrylamide --;

UNITED STATES PATENT AND TRADEMARK OFFICE
CERTIFICATE OF CORRECTION

PATENT NO. : 7,063,978 B2
APPLICATION NO. : 10/001307
DATED : June 20, 2006
INVENTOR(S) : Jerald K. Rasmussen It is certified that error appears in the above-identified patent and that said Letters Patent is hereby corrected as shown below:

Column 15
Line 38, Delete "D955" and insert in place thereof -- D-955 --;

Column 15
Line 59, Delete "(cyclobexylaminoethanesulfonic" and insert in place thereof
-- (cyclohexylaminoethanesulfonic --;

Column 17
Line 28, Delete "(DMANDM)" and insert in place thereof -- (DMA/VDM) --;

Column 17
Line 45, Delete "aziactone" and insert in place thereof -- azlactone --;

Column 17
Line 52, After the word "Probe" delete "Oligonudeotides" and insert
-- Oligonucleotides --;

Column 18
Line 39, Delete "Aziactone" and insert in place thereof -- Azlactone --;

Column 20
Line 9, In Claim 1, delete "composes" and insert in place thereof -- comprises--;

Column 21
Line 24, In Claim 25, delete "aziactone" and insert in place thereof -- azlactone--'

Signed and Sealed this

Ninth Day of January, 2007

JON W. DUDAS
*Director of the United States Patent and Trademark Office*